United States Patent [19]

Drake

[11] 4,248,799

[45] Feb. 3, 1981

[54] HYDROGENATION OF NITRILES IN AMMONIA AND WATER

[75] Inventor: Charles A. Drake, Nowata, Okla.

[73] Assignee: Phillips Petroleum Company, Bartlesville, Okla.

[21] Appl. No.: 973,768

[22] Filed: Dec. 27, 1978

[51] Int. Cl.³ .................. C07C 83/00; C07C 87/02
[52] U.S. Cl. .................................................. 564/491
[58] Field of Search ................. 260/583 K, 583 P

[56] References Cited

U.S. PATENT DOCUMENTS

| | | | |
|---|---|---|---|
| 2,449,036 | 9/1948 | Grunfeld | 260/583 K |
| 2,773,962 | 12/1956 | Heaton | 260/583 K |
| 2,790,804 | 4/1957 | Silverstone | 260/583 K |
| 3,384,666 | 5/1968 | Lichtenwalter | 260/583 K |
| 3,408,397 | 10/1968 | Feldman et al. | 260/583 K |
| 3,488,390 | 1/1970 | Carss et al. | 260/583 K |
| 3,574,754 | 4/1971 | Specken | 260/583 K |
| 3,821,305 | 6/1974 | Bartalini et al. | 260/583 K |
| 3,962,337 | 6/1976 | Drake | 260/583 K |
| 4,003,933 | 1/1977 | Drake | 260/583 K |

Primary Examiner—John F. Niebling

[57] ABSTRACT

Branched-chain aliphatic dinitriles are catalytically hydrogenated to yield branched-chain aliphatic diamines. This catalytic hydrogenation is conducted in the presence of Raney cobalt or Raney nickel, optionally promoted with Group VIB metals or reducible Group VIB metal compounds, and further in the presence of low levels of ammonia and water.

25 Claims, No Drawings

HYDROGENATION OF NITRILES IN AMMONIA AND WATER

This invention relates generally to preparation of amines from nitriles. The present invention is concerned with the catalytic hydrogenation of branched-chain aliphatic dinitriles to yield branched-chain aliphatic diamines. One aspect of the invention relates to a process for the hydrogenation of branched-chain aliphatic dinitriles in the presence of a catalyst of Raney cobalt or Raney nickel, optionally promoted with a Group VIB metal, and conducted in the presence of low levels of ammonia and water. The process of the present invention provides an increase in productivity while using conventional existing equipment and a reduction in recycling costs compared to conventional hydrogenation processes utilizing other diluents or higher levels of ammonia.

The invention is applicable to the hydrogenation of branched-chain saturated dinitriles, and is particularly applicable to the second stage of a two-stage hydrogenation of branched-chain olefinically unsaturated aliphatic dinitriles.

In the first stage, the branched-chain olefinically unsaturated aliphatic dinitrile is contacted with hydrogen under suitable hydrogenation reaction conditions in the presence of a suitable catalyst for the hydrogenation of the olefinic unsaturation. In the second stage, the saturated dinitrile from the first stage is contacted with hydrogen under suitable hydrogenation reaction conditions in the presence of Raney nickel or Raney cobalt, optionally promoted with Group VIB metals, and low levels of ammonia and water, thereby converting the branched-chain saturated dinitrile to a branched-chain saturated diamine. The two stages are preferably carried out in the order indicated. However, the order of the two stages can be reversed when desired if such a reversal is not significantly detrimental to the efficient hydrogenation of the unsaturation of the reactant.

The present process is particularly advantageous for the two-stage hydrogenation of olefinically unsaturated dinitriles of the formula:

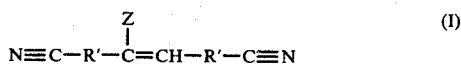

wherein each R' is independently selected from the group consisting of alkylene radicals and alkylidene radicals, and Z is an alkyl radical. Each R' will generally have 1 to 15 carbon atoms, preferably from 1 to 6 carbon atoms, and more preferably from 1 to 3 carbon atoms. Z will generally have from 1 to 15 carbon atoms, preferably from 1 to 6 carbon atoms, and more preferably from 1 to 3 carbon atoms. In general, the unsaturated dinitrile reactant of formula (I) will contain from 7 to 30 carbon atoms, preferably from 8 to 16 carbon atoms, and more preferably from 9 to 12 carbon atoms.

Representative of unsaturated reactant species of formula (I) are such compounds as 4-methyl-3-hexenedinitrile, 4-ethyl-3-hexenedinitrile, 5-methyl-r-nonenedinitrile, 5-ethyl-4-decenedinitrile, 7-methyl-6-tridecenedinitrile, 7-methyl-6-pentadecenedinitrile, 12-methyl-12-tetracosenedinitrile, 10-hexyl-9-tetracosenedinitrile, 2,3-dimethyl-3-hexenedinitrile, 2,4,6-trimethyl-3-heptenedinitrile, 4-ethyl-6,7-dimethyl-3-octenedinitrile, 2,4,6-triethyl-3-octenedinitrile, 2-ethyl-4,6-dipropyl-3-octenedinitrile, 2-methyl-4,6,8,10-tetrapropyl-3-dodecenedinitrile, 2,4,7,9,11,13,15-heptaethyl-6-hexadecenedinitrile, and mixtures of any two or more thereof.

If desired, other nitrile reactants can be present and effectively hydrogenated during the hydrogenation of the unsaturated dinitriles of formula (I). Thus, in addition to the unsaturated dinitrile reactants of formula (I), the dinitrile feedstock can contain one or more olefinically unsaturated dinitrile reactants of the formula:

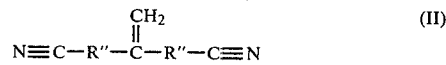

wherein each R" is independently selected from the group consisting of alkylene radicals and alkylident radicals. In general, each R" will have from 1 to 15 carbon atoms, preferably from 1 to 7 carbon atoms, and more preferably from 1 to 4 carbon atoms. The dinitriles of formula (II) will generally contain from 6 to 30 carbon atoms, preferably from 8 to 16 carbon atoms, and more preferably from 9 to 12 carbon atoms. Representative unsaturated dinitrile reactants of formula (II) include such compounds as 3-methylenehexanedinitrile, 4-methyleneheptanedinitrile, 5-methylenenonanedinitrile, 6-methyleneundecanedinitrile, 7-methylenetridecanedinitrile, 8-methylenepentadecanedinitrile, 12-methylenetetracosanedinitrile, 15-methylenenonacosanedinitrile, 2-methyl-3-methylenepentanedinitrile, 2,4-dimethyl-3-methylenepentanedinitrile, 2-methyl-4-methyleneoctanedinitrile, 2-methyl-7-ethyl-4-methyleneoctanedinitrile, 2,4,8-trimethyl-6-methylenedodecanedinitrile, 2,4,8,10-tetrapropyl-6-methylenedodecanedinitrile, 2,26-dimethyl-14-methyleneheptacosanedinitrile, and mixtures of any two or more thereof.

Nitriles having a structure other than that set forth in formulas (I) and (II) can be present during the hydrogenation of these dinitriles, if desired. Similarly, other compounds which may be found in the feed source of the dinitriles of formulas (I) and (II) can be present so long as such additional compounds do not significantly adversely affect the hydrogenation of the dinitriles of formulas (I) and (II). In a presently preferred process for the hydrogenation of dinitriles of formula (I), the dinitriles of formula (I) generally constitute at least about 0.1 weight percent, preferably at least about 5 weight percent, and more preferably at least about 10 weight percent of the total nitriles in the feedstock.

A presently preferred branched-chain unsaturated aliphatic dinitrile feedstock for employment in the practice of this invention is the dinitrile reaction product mixture obtained by the reaction of isobutylene and acrylonitrile. This dinitrile reaction product mixture generally comprises 5-methyl-4-nonenedinitrile, 2,4-dimethyl-4-octenedinitrile, 2,4-dimethyl-3-octenedinitrile, 2,4,6-trimethyl-3-heptenedinitrile, 5-methylenenonanedinitrile, 2-methyl-4-methyleneoctanedinitrile, and 2,6-dimethyl-4-methyleneheptanedinitrile. The first four named compounds in this mixture are of the type of formula (I), while the last three named compounds in this mixture are of the type of formula (II). The weight ratio of the dinitriles of formula (I) to the dinitriles of formula (II) in this mixture is generally in the range from about 10:1 to about 1:10.

The catalytic hydrogenation of the unsaturated dinitrile reactant of formula (I) results primarily in the formation of saturated diamine reaction products having the formula:

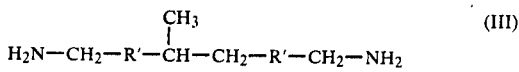
(III)

wherein R' and Z are as defined above in the discussion of the formula (I).

The catalytic hydrogenation of an unsaturated dinitrile reactant of formula (II) results primarily in the formulation of saturated diamine reaction products having the formula:

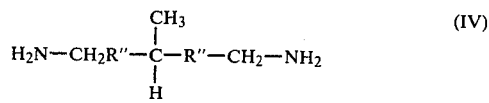
(IV)

wherein R" is as defined above in the discussion of formula (II).

The catalysts which are considered to be suitable for use in the first stage of the two-stage process for the catalytic hydrogenation of branched-chain olefinically unsaturated dinitriles according to this invention include finely divided elemental palladium, element platinum, reducible compounds of palladium or platinum, and mixtures of any two or more thereof. Suitable reducible compounds include the oxides, halides, nitrates, oxalates, acetates, carbamates, propionates, tartrates, hydroxides, and the like, and mixtures of any two or more thereof. Examples of such suitable reducible compounds include elemental palladium, palladium oxide, palladium chloride, palladium nitrate, palladium oxalate, palladium acetate, palladium hydroxide, elemental platinum, platinum oxide, platinum hydroxide, platinum acetate, platinum nitrate, platinum chloride, and the like.

The weight ratio of catalyst to unsaturated dinitrile reactant, based on the weight of the platinum or palladium contained therein, can be varied as desired. For the purpose of maintaining reasonable reaction rates under economically attractive catalyst reaction kinetics, the weight ratio of the palladium or platinum to the unsaturated dinitrile reactants is generally maintained within the range from about 0.1:100 to about 30:100, and preferably in the range from about 0.1:100 to about 20:100, but more preferably in the range from about 5:100 to about 15:100.

In the practice of this invention, it is often desirable to employ catalytic amounts of elemental palladium, elemental platinum, reducible compounds of palladium or platinum, or mixtures of any two or more thereof supported by a solid catalyst carrier which does not deleteriously affect the catalytic hydrogenation process of this invention. Such supports include, for example, carbon, kieselguhr, silica, alumina, silica-alumina, calcium carbonate, barium carbonate, asbestos, pumice, clays, and the like, and mixtures of any two or more thereof. The catalyst can be added to the catalyst support by any of the methods well known in the art. For example, the supported catalysts can be prepared by dry mixing the components or by impregnating the support with a solution or dispersion of palladium or platinum in elemental form or in the form of reducible compounds thereof or in the form of mixtures of any two or more thereof. The supported catalyst can be pretreated with hydrogen to reduce the compounds, or such reduction can be achieved easily in the hydrogenation reactor. When a support is employed, the elemental palladium and/or elemental platinum content of the catalyst system comprising the catalyst and catalyst support can be of any suitable weight percent of the total weight of catalyst components, but will generally be in the range from about 0.5 to about 50 weight percent, and preferably in the range from about 1 to about 10 weight percent, based on the weight of the total catalyst components. Presently preferred catalysts include palladium on alumina support having a palladium metal content of about 5 percent by weight based on the total weight of the catalyst and the support material, and platinum on alumina support having a platinum metal content of about 5 percent by weight based on the total weight of the catalyst and the support material. These presently preferred catalytic forms or systems, as well as other suitable catalysts, such as 5 weight percent palladium on charcoal support are commercially available.

The catalysts which are considered to be suitable for use in the second stage of the two-stage hydrogenation process of this invention for hydrogenation of the branched-chain saturated aliphatic dinitriles produced in the first stage of the process are Raney nickel, Raney cobalt, mixtures of Raney nickel and Raney cobalt and mixtures of either or both Raney nickel and Raney cobalt with at least one component selected from the group consisting of Group VIB metals and Group VIB metal compounds which are reducible by hydrogen to the corresponding elemental metal. As used herein, the terms "Raney nickel" and "Raney cobalt" refer to catalysts formed respectively by mixing nickel and aluminum or cobalt and aluminum and subsequently treating the respective mixtures with a suitable base, such as sodium hydroxide to remove the aluminum, thus leaving a highly reactive nickel or cobalt metal catalyst.

Specific examples of the group VIB metals or hydrogen-reducible metal compounds include elemental chromium, chromium acetate, chromium chloride, chromium oxide, elemental molybdenum, molybdenum hydroxide, molybdenum oxide, elemental tungsten, tungsten chloride, tungsten oxide, and the like, and mixtures of any two or more thereof.

When a mixture of Raney nickel or Raney cobalt with a Group VIB component is utilized, the weight ratio of the group VIB component to the Raney metal component can be any suitable value, but will generally be in the range from about 0.001:1 to about 0.2:1 and preferably in the range from about 0.005:1 to about 0.1:1.

The weight ratio of the second stage catalyst to the nitrile reactants can be any suitable weight ratio which will provide the desired results. For purposes of maintaining reasonable reaction rates under economically attractive catalyst reaction kinetics, the weight ratio of the total of the Raney metal and the group VIB metal, calculated as elemental metal, to the nitrile reactants will generally be in the range from about 0.01:100 to about 30:100, preferably in the range from about 0.1:100 to about 20:100, and more preferably in the range from about 5:100 to about 15:100.

Ammonia is employed in the second stage of the process of this invention in any amount which provides the desired suppression of undesirable side reaction such as the formation of secondary and tertiary amines. The amount of ammonia employed in the second stage of the process of the present invention generally ranges from about 1 to about 100 weight percent based on the amount of reactant present, preferably ranges from about 5 to about 70 weight percent and more preferably ranges from about 10 to about 50 weight percent. Although higher levels of ammonia can be used with good results, at least some of the advantages of increased productivity and reduced quantity of recycle material are lost at such higher levels of ammonia usage.

Water is employed in the second stage of the process of this invention in any amount suitable for the hydrogenation of nitrile reactants, but water will generally be present in a weight ratio of water to reactant in the range from about 1:100 to about 18:100, and preferably within a range from about 2:100 to about 15:100.

While the mixture of water and ammonia employed in the second stage of the process of this invention may be characterized generally as a diluent, it should be understood that the use of the term "diluent" in this regard should not necessarily be interpreted to mean that the mixture of water and ammonia is inert or that the mixture functions only as a diluent in the process of the present invention.

Any catalytic hydrogenation temperature can be employed which provides the desired degree of catalytic efficiency in hydrogenation of the nitrile-containing feedstock. The hydrogenation temperature in the first stage of a two-stage hydrogenation process will generally be within the range from about 30° C. to about 300° C., and preferably within the range from about 50° C. to about 100° C. The hydrogenation temperature in the second stage of a two-stage hydrogenation process will generally be in the range from about 40° C. to about 250° C., and preferably will be within the range of 60° C. to about 200° C.

The catalytic hydrogenation of the olefinic unsaturation of the reactant can be carried out in the first stage of a two-stage hydrogenation process at any suitable hydrogenation pressure wherein the olefinic unsaturation is reduced. The catalytic hydrogenation of the nitrile groups can be carried out in the second stage of a two-stage hydrogenation process at any suitable hydrogenation pressure. Generally, suitable hydrogenation pressures for each stage of a two-stage hydrogenation process are within the range from about 100 psig (0.69 MPa) to about 5000 psig (34.47 MPa), but lower or even higher hydrogenation pressures can be employed. Preferably, due to economic considerations, hydrogen pressures within the range from about 200 psig (1.38 MPa) to about 3000 psig (20.7 MPa) are employed. It may be desirable to employ higher hydrogen pressures at lower reaction temperatures to achieve the desired degree of hydrogenation within a reasonable amount of time.

Any contact time interval suited for the catalytic hydrogenation in each stage of the two-stage process can be employed in the practice of this invention. However, the time intervals economically attractive to the process are generally within the range of from about 15 minutes to about 5 hours for the first stage of a two-stage batch hydrogenation process, and generally within the range of from about 15 minutes to about 5 hours for the second stage of such a batch process. A total reaction time in the range from about 1 to about 6 hours for a two-stage hydrogenation process is presently preferred in order to insure substantially complete hydrogenation of any olefinically unsaturated bonds in the feedstock as well as substantially complete hydrogenation of the nitrile groups to primary amino groups.

If desired, the catalytic hydrogenation of either or both of the two stages can be carried out as a continuous process at any suitable liquid hourly space velocity (LHSV) which provides substantially complete hydrogenation of any olefinically unsaturated bonds of the feedstock and/or substantially complete hydrogenation of the nitrile groups to primary amino groups.

It is desirable that the first stage of the hydrogenation reaction be carried out in the presence of a suitable diluent. While any suitable diluent can be employed in the first stage, it is generally preferred that any such diluent be selected from the group consisting of unsubstituted alkanols containing from 1 to 12 carbon atoms per molecule, unsubstituted acyclic and unsubstituted cyclic ethers having 4 to 12 carbon atoms per molecule, saturated hydrocarbons having 4 to 12 carbon atoms per molecule, and mixtures of any two or more thereof. The term "unsubstituted" as used herein to signify that there are no substituents other than hydrocarbyl radicals. Examples of suitable alkanol diluents include methanol, ethanol, 2-propanol, 2-methyl-2-propanol, 2-methyl-2-butanol, 2-ethyl-2-hexanol, 2-butanol, 1-hexanol, 1-octanol, 2-decanol, 1-dodecanol, and the like and mixtures of any two or more thereof. Examples of suitable saturated hydrocarbons include butane, pentane, hexane, decane, dodecane, cyclobutane, cyclopentane, cyclohexane, cyclodecane, cyclododecane, 2-methylbutane, methylcyclopentand, 2,2,4-trimethylpentane, and mixtures of any two or more thereof. Examples of suitable ethers include diethyl ether, 1,3-dioxane, 1,4-dioxane, tetrahydrofuran, 4,4-dimethyl-1,3-dioxane, and mixtures of any two or more thereof. Any suitable weight ratio of nitrile reactants to diluent charged to the first stage hydrogenation reaction zone can be employed in the present invention, however, to facilitate handling of the reaction mixtures, the weight ratio of nitrile reactants to diluent charged to the first stage hydrogenation reaction zone will generally be within the range from about 0.001:100 to about 20:100, will preferably be in the range from about 0.1:100 to about 15:100.

Although it is presently preferred that the second stage of the two-stage hydrogenation reaction of this invention be carried out in the absence of any other diluent in addition to the ammonia and water, the reaction can be carried out in the presence of a suitable diluent. While any suitable diluent can be employed in the second stage in addition to the ammonia and water, it is preferable that any such diluent be selected from the diluents listed above for the first stage hydrogenation reaction and mixtures of any two or more thereof. The amount of any such diluent utilized in the second stage hydrogenation will generally be about 1 weight percent or more based on the weight of reactant, and will preferably be in the range from about 2 weight percent to about 50 weight percent based on the weight of reactant. Higher levels of any such diluent can result in a loss of some of the advantages of the present invention.

The first stage of the present invention provides for essentially complete hydrogenation of the olefinic unsaturation of the reactant. The second stage of the hydrogenation process of this invention provides essentially complete hydrogenation of the nitrile groups present in the reactant in the presence of low levels of ammonia and water.

The reaction effluent from the first stage can be treated in any suitable manner before introduction into the second stage. Normally, the product is separated from the first stage hydrogenation catalyst, diluent and by-products, and the thus separated product used with ammonia, water, and, if desired, an additional duluent in the second stage reaction.

Processing of the effluent from the second stage reaction of a two-stage hydrogenation process for the recovery of the desired end product, as well as any resulting reaction by-products, and any unconsumed reactants, hydrogen and/or diluents, can be carried out by any suitable conventional separation technique. In general, at the conclusion of the second stage reaction of the catalytic hydrogenation process, the reaction effluent is cooled and depressurized with the recovery, if desired, of ammonia, water and any diluent which are vented from the reaction effluent during the depressurization operation. The ammonia, water, and diluent, if present, can be returned or recycled to the appropriate reaction stage or zone, if desired. The reaction products of the second stage reaction can be separated from the catalyst by any suitable means such as by conventional filtration. The filtrate containing the at least substantially completely saturated amines can be conveniently separated from any reaction by-products or any diluent remaining in the filtrate by conventional fractionation.

The following examples are presented for their illustration of the invention and should not be construed in undue limitation thereof. Unless otherwise noted, the starting material in each of the following examples is a mixture of olefinically unsaturated dinitriles prepared by the reaction of isobutylene with acrylonitrile. This reaction mixture consists of approximately 52 weight percent 5-methylenenonanedinitrile, approximately 25 weight percent 5-methyl-4-nonenedinitrile, approximately 12 weight percent of the combination of 2,4-dimethyl-4-octenedinitrile, 2-methyl-4-methyleneoctanedinitrile and 2,4-dimethyl-3-octenedinitrile, and approximately 1 weight percent of the combination of 2,6-dimethyl-4-methyleneheptanedinitrile and 2,4,6-trimethyl-3-heptenedinitrile. For simplicity, the above reaction mixtures will be referred to hereinafter as the diadduct. Hydrogenation of both the olefinic and nitrile unsaturation of diadduct yields a saturated diamine mixture useful in the preparation of polyamides and other polymers.

EXAMPLE 1

First Stage Hydrogenation Reaction

A one liter autoclave was charged with about 30 grams (0.18 mole) of the diadduct, about 250 milliliters of methanol, about 2 grams of a catalyst consisting of about 5 weight percent palladium on an alumina support, the percentage being based on weight of the alumina support. The system was flushed with nitrogen, pressurized to about 1500 psig (10.35 MPa) with hydrogen, and heated at about 133° C. for about 2 hours. The reaction mixture was stirred throughout the reaction. The reactor was then cooled and vented and the contents filtered to remove the catalyst. The resulting filtrate was concentrated by evaporating essentially all of the diluent under vacuum. Gas-liquid chromatographic analysis of the product residue from the concentration step indicated that the product was essentially free of olefinic-unsaturation.

Second Stage Hydrogenation Reaction

A one liter autoclave was charged with about 200 grams (1.22 mole) of a saturated dinitrile mixture similar to the product mixture obtained from the first stage hydrogenation, about 25 grams of a Raney nickel catalyst containing about 3 weight percent chromium based on the total weight of the catalyst, and about 20 grams of water. The autoclave was flushed with nitrogen and charged with about 30 grams (1.76 mole) of ammonia. The autoclave was then pressured to about 750 psig (5.17 MPa) with hydrogen and heated to about 75° C. until hydrogen pressure was essentially unchanged, about 2 hours. The autoclave was then cooled and vented and the contents filtered. The resulting filtrate was concentrated by evaporation under vacuum. Gas-liquid chromatographic analysis of the product residue from the concentration step indicated complete reduction of the nitrile groups. Distillation of the product residue from the concentration step yielded about 162 grams of distillate and about 12 grams of heavies, or about 6.9 weight percent of heavies based on the weight of the total product. Since the starting material for the second stage reaction contained about 3.2 grams of heavies, only about 8.8 grams of heavies were formed in the second stage reaction or about 5.1 weight percent heavies based on the weight of the total product. As used herein and in the following examples, the term "heavies" refers to various mixtures of higher molecular weight materials boiling above about 160° C. at a pressure of about 2 millimeters of mercury. The desired products of the hydrogenation reactions of the present process boil below about 160° C. at a pressure of about 2 millimeters of mercury.

The results of the two runs from Example I demonstrate the operability for the present invention for the two-stage hydrogenation of the diadduct.

EXAMPLE II

In a control run, a one liter autoclave was charged with about 300 grams (1.22 mole) of the same saturated dinitrile mixture as was used in the second stage reaction of Example I, and about 25 grams of Raney nickel catalyst containing about 3 weight percent chromium based on the total weight of the catalyst. The autoclave was flushed with nitrogen and charged with about 30 grams (1.76 mole) of ammonia. The autoclave was then pressured to about 800 psig (5.52 MPa) with hydrogen and heated at about 75° C. until hydrogen pressure was essentially unchanged, about 5 hours. The autoclave was then cooled and vented, and the contents filtered. The filtrate was worked up as described in the second stage of Example I and a gas-liquid chromatographic analysis of the filtrate showed that essentially all of the nitrile groups had been hydrogenated. Distillation of the product residue yielded about 148.6 grams of distillate and about 28.4 grams of heavies, or about 16 weight percent of heavies based on the total product. Since the starting material for this run contained about 3.2 grams of heavies, about 25.2 grams of heavies was formed in the reaction or about 12.2 weight percent of heavies based on the total product.

This run was performed in essentially the same manner as the second stage reaction of Example I with the exception that water was not present in the reaction zone in the control run of Example II. A comparison of the results of this control run with the results of the second stage reaction in Example I demonstrates that the presence of water in the second stage reaction results in a faster reaction (i.e. about 5 hours in the control run compared with about 2 hours in the second stage reaction in the presence of water), a higher yield of distillate products (i.e. about 148.6 grams in the control run compared with about 162 grams in the second stage reaction in the presence of water), and a lower level of heavies (i.e. about 25.2 grams formed in the control run compared to about 8.8 grams formed in the second stage reaction in the presence of water).

EXAMPLE III

A series of runs was conducted in which the diadduct was utilized directly for the hydrogenation of the nitrile groups in the presence of Raney nickel catalysts without a first stage hydrogenation. The diadduct was utilized in these runs due to its ready availability. The olefinic unsaturation of the diadduct was incompletely hydrogenated and was not considered in product evaluation.

In each of runs 1, 2, 3, 4, 5, 6, 7 8 and 9, a one liter autoclave was charged with about 200 grams (1.53 mole) of diadduct, a Raney nickel catalyst and water (runs 1, 2, 3, 4, 5, 6 and 7). The system was flushed with nitrogen and charged with either about 30 grams (1.76 mole) of ammonia in runs 1, 2 and 7, or about 100 grams (5.88 mole) of ammonia in runs 3, 4, 5, 6, 8 and 9; pressured with hydrogen to about 750 psig (5.17 MPa) in runs 1, 2, 3, 4 and 7, to about 1500 psig (10.34 MPa) in runs 5, 6 and 8, and to about 800 psig (5.52 MPa) in run 9; and heated in runs 1, 2, 3, 4, 5, 6 and 7 to about 80° C. for a reaction period of about 2 hours or until hydrogen pressure was essentially unchanged. The autoclave was then cooled and vented, and the contents filtered. The resulting filtrate was concentrated by evaporating the water under vacuum. The product was analyzed by gas-liquid chromatography and then fractionally distilled to separate the volatile product from the heavies. The catalyst compositions, the quantities of catalyst, ammonia and water used in the hydrogenation reactions, and the amounts of heavies found in the reaction products for each of runs 1 through 9 of Example III are shown in Table 1.

water in the reaction mixture resulted in either little hydrogenation, as shown in run 8, or a high heavies level with incomplete nitrile reduction, as shown in run 9, thus demonstrating the critical nature of the presence of water in the reaction mixture in the present invention. Essentially complete reduction of the nitrile groups was found to have occurred in runs 1 through 7.

EXAMPLE IV

The following comparative run illustrates the Raney nickel catalyzed hydrogenation of diadduct in the presence of methanol or a diluent. A one liter autoclave was charged with about 237 grams of methanol, about 10 grams of Raney nickel, and about 80 grams (0.49 mole) of diadduct. The autoclave was flushed with nitrogen and charged with about 190 grams (11.2 mole) of ammonia. The autoclave was then pressured to about 1200 psig (8.27 MPa) with hydrogen and heated to about 130° C. for about two hours. The autoclave was then cooled and vented and the contents filtered. The filtrate was concentrated by evaporating the diluent under vacuum. Fractional distillation of the product gave about 78 grams of distillate and about 4 grams of heavies, or about 4.9 weight percent of heavies based on the total product. Gas-liquid chromatographic analysis of the main fraction of the distillate showed that essentially complete hydrogenation of the nitrile groups had occurred.

A comparison of this run with run 3 of Example III illustrates the advantages of the process of the present invention. The run described in Example IV used about 80 grams of diadduct per about 517 grams of total charge, or about 15 weight percent diadduct, while run 3 of Example III used about 200 grams diadduct per about 345 grams of total charge, about 58 weight percent diadduct. The run of Example IV contained about 237 grams of methanol and about 190 grams of ammonia (a total of about 83 weight percent of the total autoclave charge) which could be recycled while run 3 of Example III contained only about 100 grams of ammonia and about 20 grams of water (a total of about 35 weight percent of the total autoclave charge) which could be recycled. Therefore, the process of the present inven-

TABLE I

| Run No. | Raney Nickel Catalyst Promoter[a] | Hydrogen Pressure, psig (MPa) | Total Catalyst Weight, g. | Ammonia, g. | Water, g. | Heavies, Weight %[b] | Total Product, g. | Heavies, g. |
|---|---|---|---|---|---|---|---|---|
| 1 | Chromium | 750(5.2) | 25 | 30 | 20 | 7 | 171.0 | 12.0 |
| 2 | Chromium | 750(5.2) | 10 | 30 | 20 | 7 | 172.0 | 12.0 |
| 3 | Chromium | 750(5.2) | 25 | 100 | 20 | 5.1 | 185.5 | 9.5 |
| 4[c] | Chromium | 750(5.2) | 25 | 100 | 20 | 2.8 | 178.0 | 5.0 |
| 5[d] | Chromium | 1500(10.4) | 15 | 100 | 20 | 4 | 188.5 | 7.5 |
| 6[d] | None | 1500(1004) | 15 | 100 | 20 | 2.3 | 186.8 | 4.3 |
| 7 | Chromium | 750(5.2) | 25 | 30 | 40 | 10.4 | 183.0 | 19.0 |
| 8[d] | Chromium | 1500(10.4) | 15 | 100 | None | (e) | (e) | (e) |
| 9[f] | Chromium | 800(5.5) | 25 | 100 | None | 17.3 | 191.0 | 33.0 |

[a]The promoted catalysts contained about 3 weight percent chromium based on the total weight of catalyst.
[b]Weight percent heavies based on weight of total reaction product.
[c]The diadduct was purified by contact with alumina.
[d]The diadduct was purified by double contact with alumina.
[e]Little hydrogenation occurred.
[f]The reaction product contained about 10 weight percent nitrile groups.

The results of these runs demonstrate operability of the present invention using chromium-promoted Raney nickel in runs 1 through 5 and unpromoted Raney nickel in run 6. Increasing the amount of water in the reaction mixture from about 10 weight percent of the diadduct in run 1 to about 20 weight percent of the diadduct in run 7 resulted in a substantial increase in the heavies level of the reaction product. The absence of tion is shown to yield a higher productivity and to provide a lower weight percent of material for recycle than is provided by a typical hydrogenation run using a diluent as exemplified in Example IV.

EXAMPLE V

A series of runs was conducted in which diadduct was hydrogenated in the presence of chromium-promoted Raney nickel, ammonia and water, and the catalyst from each hydrogenation run was reused in the next following run with the addition of small amounts of fresh catalyst.

In each of these runs a one liter autoclave, fitted with a sintered metal filter on the end of a diptube extending to the bottom of the autoclave to allow product removal while retaining the catalyst in the autoclave, was employed. The autoclave was charged with about 200 grams (1.23 mole) of diadduct, about 20 grams of water and a Raney nickel catalyst containing about 3 weight percent chromium based on the total weight of the catalyst. In the first of these runs, designated as run 11, the autoclave was charged with about 25 grams of the chromium-promoted Raney nickel catalyst, and in each run thereafter, runs 12, 13 and 14, the autoclave was charged with an additional quantity of about 5 grams of the same catalyst through a second open diptube. The system was flushed with nitrogen and charged with about 100 grams (5.88 mole) of ammonia, pressured to about 750 psig (5.17 MPa) with hydrogen and heated to about 80° C. for about a 2-hour reaction period or until hydrogen pressure was essentially unchanged.

The autoclave was then cooled and vented, and the liquid contents were removed therefrom through the filter-terminated diptube with the solid catalyst remaining in the autoclave. The liquid filtrate was worked up as previously described in Example III and the catalyst remaining in the autoclave was reused in the next following run.

Results of these runs 11 through 14 are presented in Table II.

TABLE II

| Run No. | Heavies, [a] Weight Percent |
|---|---|
| 11 | 4.8 |
| 12 | 7.1 |
| 13 | 5.8 |
| 14 | 6.5 |

[a] Weight percent heavies based on the total weight of reaction product.

The results of runs 11, 12, 13 and 14 demonstrate that the catalyst from the hydrogenation process of the present invention can be recycled with the addition of some fresh catalyst with essentially no increase in the weight percent of heavies in the reaction product.

EXAMPLE VI

A series of runs was conducted in which the diadduct was hydrogenated over Raney cobalt catalyst (runs 15, 17, 18, 19, 20 and 21) or a Raney cobalt catalyst containing about 4 weight percent molybdenum promoter with the percentage of molybdenum based on the total catalyst weight (run 16). In each run a one liter autoclave was charged with about 200 grams (1.23 mole) of the diadduct, the catalyst, about 20 grams of water (runs 15, 16, 17 and 20), and 2-methyl-2-propanol (runs 17 and 19). The system was flushed with nitrogen and charged with either about 30 grams of ammonia (1.76 mole) in runs 15 and 18, about 100 grams of ammonia (5.88 mole) in runs 16, 17, 19, and about 300 grams (17.64 mole) of ammonia in runs 20 and 21. The system was pressured to either about 750 psig (5.17 MPa) in runs 15, 16 and 18 or to about 1500 psig (10.34 MPa) in runs 17, 19, 20 and 21 with hydrogen and heated to about 80° C. for a reaction period of about two hours or until hydrogen pressure was essentially unchanged. The autoclave was then cooled and vented, and the contents thereof filtered. The resulting filtrate was worked up as previously described in Example III. The quantities used in the hydrogenation runs and the amounts of heavies present in the reaction product are presented in Table III.

TABLE III

| Run No. | Total Catalyst,[a] g. | Hydrogen Pressure, Psig (MPa) | Promotor | Ammonia, g. | Water, g. | Heavies,[b] Weight Percent |
|---|---|---|---|---|---|---|
| 15 | 25 | 750(5.17) | — | 30 | 20 | 5.7 |
| 16 | 25 | 750(5.17) | Mo | 100 | 20 | 6.5 |
| 17 [c] | 20 | 1500(10.34) | — | 100 | 20 | 2.8 |
| 18 | 25 | 750(5.17) | — | 30 | none | 13.3 |
| 19 [d] | 20 | 1500(10.34) | — | 100 | none | 10.6 |
| 20 | 20 | 1500(10.34) | — | 300 | 20 | 2.3 |
| 21 | 20 | 1500(10.34) | — | 300 | none | 14.6 |

[a] Raney cobalt catalyst including promotor in run 16.
[b] Weight percent heavies based on total weight of product.
[c] The reaction mixture also contains 200 g. 2-methyl-2-propanol.
[d] The reaction mixture also contains 20 g. 2-methyl-2-propanol.

The results of runs 15, 16 and 17 demonstrate operability of the present invention for the hydrogenation of nitrile groups in the presence of Raney cobalt or Raney cobalt promoted with about 4 weight percent molybdenum and low levels of ammonia and water. A comparison of run 15 with run 18 shows that in the absence of water, the amount of heavies in the product increases from about 5.7 to about 13.3 weight percent based on the total weight of the product. The results of run 19 indicate that the substitution of 2-methyl-2-propanol for water in the reaction resulted in a high level of heavies in the product and required a longer reaction time of about 7 hours to complete hydrogenation than was required in invention runs 15 and 16 which required about 3 hours and about 2 hours respectively to complete hydrogenation. Although the results of run 17 indicate that an additional diluent such as 2-methyl-2-propanol can be present in addition to the components of the preferred embodiment of this invention, i.e. a mixture which consists essentially of ammonia and water, the advantages of this invention for reduced recycling costs are best utilized in the absence of additional diluents added to the ammonia and water. A comparison of runs 20 and 21 shows that at higher ammonia levels the presence of water decreases the heavies level in the product in the same manner as shown at lower ammonia levels, however, the advantages of this invention for high productivity and low amounts of recycled material are somewhat reduced by the utilization of higher ammonia levels in the presence of water even though significantly low levels of heavies are present in the reaction product.

A comparison of run 16 with U.S. Pat. No. 3,488,390, which discloses the use of adiponitrile as reactant and a different cobalt catalyst, illustrates certain advantages of this invention over the prior art. Run 16 used about 200 grams of diadduct per about 345 grams of total autoclave charge, i.e. about 200 grams of diadduct, about 100 grams (5.88 mole) of ammonia, about 20 grams of water, and about 25 grams of catalyst, or about 58 weight percent diadduct based on U.S. Pat. No. 3,488,390 would use about 200 grams of diadduct per about 705 grams of total autoclave charge, i.e. about 200 grams of diadduct, about 460 grams (27 mole) of ammonia, about 20 grams of water, and about 25 grams of catalyst, or about 28 weight percent diadduct based on the total autoclave charge. Additionally, run 16 contained about 120 grams of ammonia and water, or a total about 35 weight percent of the total autoclave charge, for recycling while a run based on the teaching of U.S. Pat. No. 3,488,390 would contain about 480 grams of ammonia and water, or a total of 68 weight percent of the total autoclave charge for recycling. Therefore, the process of the present invention utilizes a higher percentage of reactant in the reactor charge and smaller quantities of materials for recycling than would be required by a hydrogenation process based on the teaching of the prior art as exemplified by U.S. Pat. No. 3,488,390.

The invention is not to be construed as limited to the particular forms disclosed herein, since these are to be regarded as illustrative rather than restrictive. Reasonable variations and modifications are possible within the scope of the foregoing disclosure and the appended claims to the invention.

That which is claimed is:

1. A process for the catalytic hydrogenation of at least one aliphatic dinitrile to produce primary diamines, comprising:
contacting at least one said aliphatic dinitrile, in the substantial absence of unsubstituted alkanols containing from 1 to 12 carbon atoms per molecule, unsubstituted tertiary aliphatic alcohols having 4 to 12 carbon atoms per molecule, unsubstituted acyclic and unsubstituted cyclic ethers having 4 to 12 carbon atoms per molecule, saturated hydrocarbons having 4 to 12 carbon atoms per molecule, and mixtures thereof, with hydrogen, ammonia, water and a catalyst under suitable hydrogenation conditions, said catalyst being selected from the group consisting of Raney nickel, Raney cobalt, mixtures of Raney nickel and Raney cobalt, mixtures of Raney nickel with at least one component selected from the group consisting of elemental Group VIB metals and Group VIB metal compounds reducible by hydrogen to the corresponding Group VIB metal under said hydrogenation conditions, mixtures of Raney cobalt with at least one component selected from the group consisting of Group VIB metals and Group VIB metal compounds reducible by hydrogen to the corresponding Group VIB metals under said hydrogenation conditions, and mixtures of Raney nickel and Raney cobalt and at least one component selected from the group consisting of Group VIB metals and Group VIB metal compounds reducible by hydrogen to the corresponding Group VIB metals under said hydrogenation conditions, said water being present in a weight ratio of said water to said at least one aliphatic dinitrile in the range from about 1:100 to about 18:100, and said ammonia being present in an amount in the range from about 1 to about 100 weight percent based on the amount of said at least one aliphatic dinitrile.

2. A process in accordance with claim 1 wherein the weight ratio of water to said at least one aliphatic dinitrile is in the range from about 2:100 to about 15:100.

3. A process in accordance with claim 1 wherein said catalyst is Raney nickel.

4. A process in accordance with claim 1 wherein said catalyst is a mixture of Raney nickel and at least one component selected from the group consisting of elemental Group VIB metals and Group VIB metal compounds reducible to hydrogen to the corresponding Group VIB metals under said hydrogenation conditions.

5. A process in accordance with claim 1 wherein said catalyst is a mixture of Raney nickel and chromium.

6. A process in accordance with claim 1 wherein said catalyst is Raney cobalt.

7. A process in accordance with claim 1 wherein said catalyst is a mixture of Raney cobalt and molybdenum.

8. A process in accordance with claim 1 wherein said suitable hydrogenation conditions comprise a temperature in the range from about 40° C. to about 250° C. and a hydrogen pressure in the range from about 100 psig (0.69 MPa) to about 5000 psig (34.47 MPa).

9. A process in accordance with claim 1 wherein said at least one aliphatic dinitrile comprises at least one dinitrile of the formula

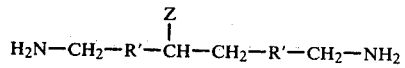

wherein each R′ is independently selected from the group consisting of alkylene radicals and alkylidene radicals and has from 1 to about 15 carbon atoms, and Z is an alkyl radical having from 1 to about 15 carbon atoms.

10. A process for the catalytic hydrogenation of at least one nitrile to produce primary amines, comprising contacting said at least one nitrile, in the substantial absence of unsubstituted alkanols containing from 1 to 12 carbon atoms per molecule, unsubstituted tertiary aliphatic alcohols having 4 to 12 carbon atoms per molecule, unsubstituted acyclic and unsubstituted cyclic ethers having 4 to 12 carbon atoms per molecule, saturated hydrocarbons having 4 to 12 carbon atoms per molecule, and mixtures thereof, with hydrogen, ammonia, water and a catalyst under suitable hydrogenation conditions, said catalyst being selected from the group consisting of Raney nickel, mixtures of Raney nickel and Raney cobalt and mixtures of Raney nickel with at least one component selected from the group consisting of elemental Group VIB metals and Group VIB metal compounds reducible by hydrogen to the corresponding Group VIB metals under said hydrogenation conditions, said water being present in a weight ratio of said water to said at least one nitrile in the range from about 1:100 to about 18:100, and said ammonia being present in an amount in the range from about 1 to about 100 weight percent based on the amount of said at least one nitrile.

11. A process in accordance with claim 10 wherein the weight ratio of water to said at least one nitrile is in the range from about 2:100 to about 15:100.

12. A process in accordance with claim 10 wherein said catalyst is Raney nickel.

13. A process in accordance with claim 10 wherein said catalyst is a mixture of Raney nickel and at least one component selected from the group consisting of elemental Group VIB metals and Group VIB metal compounds reducible by hydrogen to the corresponding Group VIB metals under said hydrogenation conditions.

14. A process in accordance with claim 10 wherein said catalyst is a mixture of Raney nickel and chromium.

15. A process in accordance with claim 10 wherein said suitable hydrogenation conditions comprise a temperature in the range from about 40° C. to about 250° C.

and a hydrogen pressure in the range from about 100 psig (0.69 MPa) to about 5000 psig (34.47 MPa).

16. A process in accordance with claim 10 wherein said at least one nitrile is of the formula

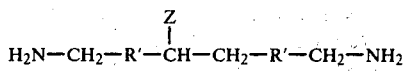

wherein each R' is independently selected from the group consisting of alkylene radicals and alkylidene radicals and has from 1 to about 15 carbon atoms, and Z is an alkyl radical having from 1 to about 15 carbon atoms.

17. A process for the catalytic hydrogenation of an olefinically unsaturated dinitrile feedstock comprising at least one unsaturated branched-chain aliphatic dinitrile compound of the formula

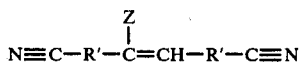

wherein each R' is independently selected from the group consisting of alkylene radicals and alkylidene radicals and has from 1 to about 15 carbon atoms, and Z is an alkyl radical having from 1 to about 15 carbon atoms; which process comprises:
(a) contacting said feedstock in a first stage reaction zone with hydrogen, a first diluent and a first catalyst under suitable first stage hydrogenation conditions to thereby effect the at least substantially complete hydrogenation of the olefinic unsaturation of said compound so as to form a first reaction effluent;
(b) removing said first diluent from said thus formed first reaction effluent so as to form an intermediate dinitrile product at least substantially free of olefinic unsaturation and at least substantially free of said first diluent; and
(c) contacting said thus formed intermediate dinitrile product in a second stage reaction zone, in the substantial absence of unsubstituted alkanols containing from 1 to 12 carbon atoms per molecule, unsubstituted tertiary aliphatic alcohols having 4 to 12 carbon atoms per molecule, unsubstituted acyclic and unsubstituted cyclic ethers having 4 to 12 carbon atoms per molecule, saturated hydrocarbons having 4 to 12 carbon atoms per molecule, and mixtures thereof, with hydrogen, ammonia, water and a second catalyst under suitable second stage hydrogenation reaction conditions to thereby effect the at least substantially complete conversion of nitrile groups in said intermediate dinitrile product to primary amine groups, said catalyst being selected from the group consisting of Raney nickel, Raney cobalt, mixtures of Raney nickel and Raney cobalt, mixtures of Raney nickel with at least one component selected from the group consisting of elemental Group VIB metals and Group VIB metal compounds reducible by hydrogen to the corresponding Group VIB metals under said second stage hydrogenation reaction conditions, mixtures of Raney cobalt with at least one component selected from the group consisting of Group VIB metals and Group VIB metal compounds reducible by hydrogen to the corresponding Group VIB metals under said second stage hydrogenation reaction conditions, and mixtures of Raney nickel and Raney cobalt and at least one component selected from the group consisting of Group VIB metals and Group VIB metal compounds reducible by hydrogen to the corresponding Group VIB metals under said second stage hydrogenation reaction conditions said water being present in a weight ratio of said water to said intermediate dinitrile product in step (c) in the range from about 1:100 to about 18:100, and said ammonia being present in step (c) in an amount in the range from about 1 to about 100 weight percent based on the amount of said intermediate dinitrile product.

18. A process in accordance with claim 17 wherein the weight ratio of water of said intermediate dinitrile product in step (c) is in the range from abou 2:100 to about 15:100.

19. A process in accordance with claim 17 wherein said second catalyst is Raney nickel.

20. A process in accordance with claim 17 wherein said second catalyst is a mixture of Raney nickel and at least one component selected from the group consisting of elemental Group VIB metals and Group VIB metal compounds reducible by hydrogen to the corresponding Group VIB metals under said second stage hydrogenation reaction conditions.

21. A process in accordance with claim 17 wherein said second catalyst is a mixture of Raney nickel and chromium.

22. A process in accordance with claim 17 wherein said second catalyst is Raney cobalt.

23. A process in accordance with claim 17 wherein said second catalyst is a mixture of Raney cobalt and molybdenum.

24. A process in accordance with claim 17 wherein said second stage hydrogenation reaction conditions comprise a temperature in the range from about 40° C. to about 250° C. and a hydrogen pressure in the range from about 100 psig (0.69 Mpa) to about 5000 psig (34.47 MPa).

25. A process for the catalytic hydrogenation of at least one nitrile to produce primary amines, comprising contacting said at least one nitrile, in the substantial absence of unsubstituted alkanols containing from 1 to 12 carbon atoms per molecule, unsubstituted tertiary aliphatic alcohols having 4 to 12 carbon atoms per molecule, unsubstituted acyclic and unsubstituted cyclic ethers having 4 to 12 carbon atoms per molecule, saturated hydrocarbons having 4 to 12 carbon atoms per molecule, and mixtures thereof, with hydrogen, a diluent consisting essentially of water and ammonia, and a catalyst under suitable hydrogenation conditions, said catalyst being selected from the group consisting of Raney nickel, Raney cobalt, mixtures of Raney nickel and Raney cobalt, mixtures of Raney nickel with at least one component selected from the group consisting of elemental Group VIB metals and Group VIB metal compounds reducible by hydrogen to the corresponding Group VIB metal under said hydrogenation conditions, mixtures of Raney cobalt with at least one component selected from the group consisting of Group VIB metals and Group VIB metal compounds reducible by hydrogen to the corresponding Group VIB metals under said hydrogenation conditions, and mixtures of Raney nickel and Raney cobalt and at least one component selected from the group consisting of Group VIB metals and Group VIB metal compounds reducible by hydrogen to the corresponding Group VIB metals under said hydrogenation conditions, said water being present in a weight ratio of said water to said at least one nitrile in the range from about 1:100 to about 18:100, and said ammonia being present in an amount in the range from about 1 to about 100 weight percent based on the amount of said at least one nitrile.

* * * * *